(12) United States Patent
Nesvadba et al.

(10) Patent No.: US 9,701,762 B2
(45) Date of Patent: Jul. 11, 2017

(54) HYBRID PHOTOINITIATORS

(71) Applicant: BASF SE, Ludwigshafen (DE)

(72) Inventors: Peter Nesvadba, Marly (CH);
Jean-Luc Birbaum, Binningen (CH);
Yvonne Pilak, Grenzach-Wyhlen (DE);
Bruno Spony, Wahlbach (FR); Florian Ziegler, Witterswil (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/436,694

(22) PCT Filed: Oct. 16, 2013

(86) PCT No.: PCT/EP2013/071582
§ 371 (c)(1),
(2) Date: Apr. 17, 2015

(87) PCT Pub. No.: WO2014/060450
PCT Pub. Date: Apr. 24, 2014

(65) Prior Publication Data
US 2016/0168279 A1   Jun. 16, 2016

Related U.S. Application Data

(60) Provisional application No. 61/715,843, filed on Oct. 19, 2012.

(30) Foreign Application Priority Data

Oct. 19, 2012   (EP) .................................... 12189152

(51) Int. Cl.
*C08F 2/50*    (2006.01)
*C08F 2/46*    (2006.01)
(Continued)

(52) U.S. Cl.
CPC ............... *C08F 2/50* (2013.01); *C07C 67/14* (2013.01); *C07C 69/003* (2013.01);
(Continued)

(58) Field of Classification Search
CPC ......... C08F 2/50; C07C 67/14; C07C 69/003; C07C 69/716; C09D 4/00
(Continued)

(56) References Cited

U.S. PATENT DOCUMENTS 3,844,916 A   10/1974 Gaske
3,957,512 A   5/1976 Kleeberg et al.
(Continued)

FOREIGN PATENT DOCUMENTS

CA   1117691 A1   2/1982
CA   2041191 A1   10/1991
(Continued)

OTHER PUBLICATIONS

International Search Report for PCT/EP2013/071582 mailed Nov. 25, 2013.
(Continued)

*Primary Examiner* — Jessica E Whiteley
(74) *Attorney, Agent, or Firm* — Marshall, Gerstein & Borun LLP

(57) ABSTRACT

Compounds of the formula I

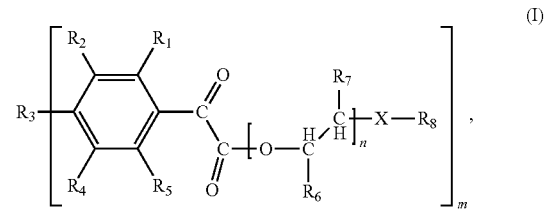

wherein
m is 1 or 2;
$R_1$, $R_2$, $R_4$ and $R_5$ independently of one another are hydrogen, $C_1$-$C_4$alkyl, $C_5$-$C_7$ cycloalkyl, phenyl, $C_1$-$C_4$alkoxy, $C_5$-$C_7$cycloalkoxy or phenoxy;
$R_3$, if m is 1, has one of the meanings as given above for $R_1$, $R_2$, $R_4$ and $R_5$;
$R_3$, if m is 2, is a divalent group;
$R_6$ is hydrogen or $C_1$-$C_4$alkyl;
$R_7$ is hydrogen, and if $R_6$ is hydrogen then $R_7$ may additionally be $C_1$-$C_4$alkyl;
$R_8$ is group A or B

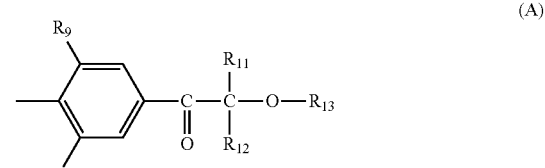

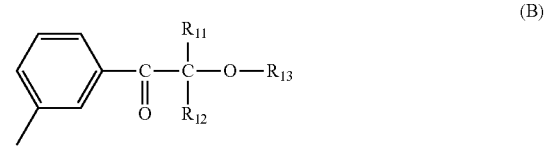

X is O, O—$CH_2$— or —O(CH$R_{14}$)—;
n is 0-10;
provided that
(i) if n is 0, and X is O, then $R_8$ is a group A;
(ii) if n is other than 0, then X is O and $R_8$ is the group A;
$R_9$ and $R_{10}$ independently of one another are hydrogen or $C_1$-$C_4$alkyl;
$R_{11}$ and $R_{12}$ independently of one another are $C_1$-$C_4$alkyl or form together with the C atom to which they are attached a 5 to 7 membered saturated carbocyclic ring;
(Continued)

$R_{13}$ is hydrogen, $C_1$-$C_4$alkyl, $C_5$-$C_7$cycloalkyl, 2-tetrahydropyranyl or $Si(C_1$-$C_4alkyl)_3$;

$R_{14}$ is a group A'

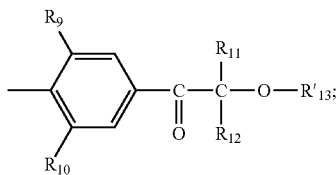

(A')

and $R'_{13}$ has one of the meanings as given for $R_{13}$ or is the group C

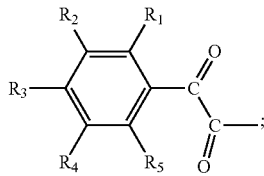

(C)

are effective photoinitiator compounds.

13 Claims, No Drawings

(51) Int. Cl.

| | |
|---|---|
| C08G 61/04 | (2006.01) |
| C07C 69/738 | (2006.01) |
| C07C 69/616 | (2006.01) |
| C07C 67/14 | (2006.01) |
| C07C 69/003 | (2006.01) |
| C07C 69/716 | (2006.01) |
| C09D 4/00 | (2006.01) |

(52) U.S. Cl.
CPC .......... C07C 69/616 (2013.01); C07C 69/716 (2013.01); C07C 69/738 (2013.01); C09D 4/00 (2013.01)

(58) Field of Classification Search
USPC ........ 522/8, 7, 68, 6, 71, 189, 184, 1; 520/1
See application file for complete search history.

(56) References Cited

U.S. PATENT DOCUMENTS

| | | |
|---|---|---|
| 4,287,039 A | 9/1981 | Buethe et al. |
| 4,318,791 A | 3/1982 | Felder et al. |
| 4,339,566 A | 7/1982 | Rosenkranz et al. |
| 4,384,056 A | 5/1983 | Schmidt et al. |
| 4,496,447 A * | 1/1985 | Eichler .................. C07C 45/28 522/103 |
| 4,575,330 A | 3/1986 | Hull |
| 4,753,817 A | 6/1988 | Meixner et al. |
| 4,950,581 A | 8/1990 | Koike et al. |
| 5,013,768 A | 5/1991 | Kiriyama et al. |
| 5,186,846 A | 2/1993 | Brueckmann et al. |
| 5,376,459 A | 12/1994 | Christner et al. |
| 5,482,649 A | 1/1996 | Meixner et al. |
| 5,538,548 A | 7/1996 | Yamazaki |
| 5,587,404 A | 12/1996 | Kröner et al. |
| 5,620,751 A | 4/1997 | Brindoepke et al. |
| 5,734,002 A | 3/1998 | Reich et al. |
| 5,922,473 A | 7/1999 | Muthiah et al. |
| 6,294,592 B1 | 9/2001 | Herrmann et al. |
| 6,306,555 B1 | 10/2001 | Schulz et al. |
| 8,742,175 B2 | 6/2014 | Zhang et al. |

FOREIGN PATENT DOCUMENTS

| | | |
|---|---|---|
| CA | 2159265 A1 | 3/1996 |
| CN | 103709036 A | 4/2014 |
| DE | 2308830 A1 | 8/1974 |
| DE | 2936039 A1 | 4/1981 |
| DE | 4013358 A1 | 10/1991 |
| DE | 4228514 A1 | 3/1994 |
| DE | 19700064 A1 | 7/1997 |
| DE | 19727767 A1 | 1/1999 |
| EP | 7086 A1 | 1/1980 |
| EP | 012339 A1 | 6/1980 |
| EP | 033896 A1 | 8/1981 |
| EP | 041125 A1 | 12/1981 |
| EP | 126541 A1 | 11/1984 |
| EP | 245639 A2 | 11/1987 |
| EP | 280222 A2 | 8/1988 |
| EP | 339841 A2 | 11/1989 |
| EP | 438123 A2 | 7/1991 |
| EP | 636669 A2 | 2/1995 |
| EP | 678534 A1 | 10/1995 |
| EP | 704469 A2 | 4/1996 |
| EP | 956280 A1 | 11/1999 |
| GB | 2180358 A | 3/1987 |
| JP | 2009143972 A | 7/2009 |
| JP | 2010287450 A | 12/2010 |
| WO | WO-98/33761 | 8/1998 |
| WO | WO-99/03930 A1 | 1/1999 |
| WO | WO-00/10974 A2 | 3/2000 |
| WO | WO-00/20517 A2 | 4/2000 |
| WO | WO 01/42313 | 6/2001 |
| WO | WO-03/064061 A1 | 8/2003 |
| WO | WO-2004/074328 A1 | 9/2004 |
| WO | WO-2004/099262 A1 | 11/2004 |
| WO | WO-2006/008251 A2 | 1/2006 |
| WO | WO-2010108862 A1 | 9/2010 |
| WO | WO-2012062041 A1 | 5/2012 |

OTHER PUBLICATIONS

Notice of Preliminary Rejection (with English translation), Korean patent application No. 10-2015-7012680, issued Sep. 28, 2016.
Notification of Reasons for Refusal (English translation), Japanese patent application No. 2015-537235, mailed Jul. 19, 2016.

* cited by examiner

HYBRID PHOTOINITIATORS

CROSS-REFERENCE TO RELATED APPLICATIONS

This application is a national stage application (under 35 U.S.C. §371) of PCT/EP2013/071582, filed Oct. 16, 2013, which claims benefit of European Application No. 12189152.7, filed Oct. 19, 2012, and U.S. Application No. 61/715,843, filed Oct. 19, 2012, all of which are incorporated herein by reference in their entirety.

Object of the present invention are novel hybrid photoinitiators and their use for polymerization (curing) of radically polymerizable compositions triggered by electromagnetic or particulate radiation.

Radiation curing of large variety of radically polymerizable compositions is a well-known technique.

Esters of phenylglyoxylic acid and α-hydroxy compounds are well-known photoinitiators as for example disclosed in EP956280 or U.S. Pat. No. 4,318,791.

The increasing concerns about health and environmental aspects of chemicals require replacement of volatile photoinitiators with new ones having lower volatility and higher activity.

We have now discovered that the hitherto unknown molecular combinations of phenylglyoxylic acid compounds with α-hydroxyketone photoinitiators represent highly efficient novel photoinitiators with low volatility and outstanding curing properties.

Subject of the invention therefore are compounds of the formula (I)

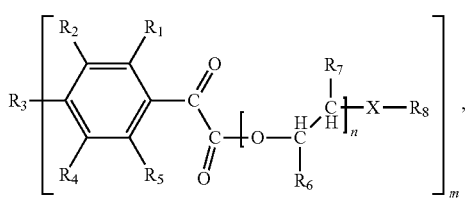

(I)

wherein
m is 1 or 2;
$R_1$, $R_2$, $R_4$ and $R_5$ independently of one another are hydrogen, $C_1$-$C_4$alkyl, $C_5$-$C_7$ cycloalkyl, phenyl, $C_1$-$C_4$alkoxy, $C_5$-$C_7$cycloalkoxy or phenoxy;
$R_3$, if m is 1, has one of the meanings as given above for $R_1$, $R_2$, $R_4$ and $R_5$;
$R_3$, if m is 2, is a divalent group;
$R_6$ is hydrogen or $C_1$-$C_4$alkyl;
$R_7$ is hydrogen, and if $R_6$ is hydrogen then $R_7$ may additionally be $C_1$-$C_4$alkyl;
$R_8$ is group A or B

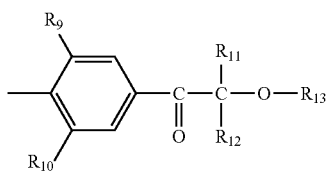

(A)

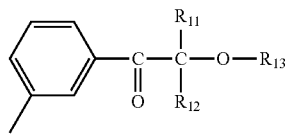

(B)

X is O, O—CH$_2$— or —O(CHR$_{14}$)—;
n is 0-10;
  provided that
  (i) if n is 0, and X is O, then $R_8$ is a group A;
  (ii) if n is other than 0, then X is O and $R_8$ is the group A;
$R_9$ and $R_{10}$ independently of one another are hydrogen or $C_1$-$C_4$alkyl;
$R_{11}$ and $R_{12}$ independently of one another are $C_1$-$C_4$alkyl or form together with the C atom to which they are attached a 5 to 7 membered saturated carbocyclic ring;
$R_{13}$ is hydrogen, $C_1$-$C_4$alkyl, $C_5$-$C_7$cycloalkyl, 2-tetrahydropyranyl or Si($C_1$-$C_4$alkyl)$_3$;
$R_{14}$ is a group A'

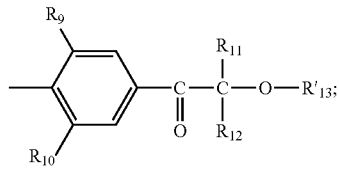

(A')

and
$R'_{13}$ has one of the meanings as given for $R_{13}$ or is the group C

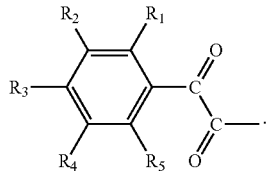

(C)

$C_1$-$C_4$alkyl is linear or branched. Examples are methyl, ethyl, propyl, isopropyl, n-butyl, sec-butyl, isobutyl, tert-butyl, in particular methyl.

$C_5$-$C_7$cycloalkyl is for example cyclopropyl, cyclopentyl, cyclohexyl, cycloheptyl, especially cyclopentyl and cyclohexyl, preferably cyclohexyl.

$C_1$-$C_4$alkoxy is linear or branched and is for methoxy, ethoxy, propoxy, isopropoxy, n-butyloxy, sec-butyloxy, isobutyloxy or tert-butyloxy, in particular methoxy.

$C_5$-$C_7$cycloalkoxy
$R_1$, $R_2$, $R_4$ and $R_5$ for example independently of one another are hydrogen, $C_1$-$C_4$alkyl, $C_5$-$C_7$ cycloalkyl, $C_1$-$C_4$alkoxy, or $C_5$-$C_7$cycloalkoxy;
or $R_1$, $R_2$, $R_4$ and $R_5$ for example independently of one another are hydrogen, $C_1$-$C_4$alkyl, $C_5$-$C_7$ cycloalkyl or phenyl;
or $R_1$, $R_2$, $R_4$ and $R_5$ for example independently of one another are hydrogen, $C_1$-$C_4$alkyl or $C_5$-$C_7$ cycloalkyl;
or $R_1$, $R_2$, $R_4$ and $R_5$ for example independently of one another are hydrogen or $C_1$-$C_4$alkyl, in particular hydrogen.

The preferences and examples for $R_3$, if m is 1, are as given above for $R_1$, $R_2$, $R_4$ and $R_5$; $R_9$ and $R_{10}$ independently of one another are hydrogen or $C_1$-$C_4$alkyl, in particular hydrogen.

$R_{11}$ and $R_{12}$ independently of one another are $C_1$-$C_4$alkyl or form together with the C atom to which they are attached a 5 to 7 membered saturated carbocyclic ring.

In particular $R_{11}$ and $R_{12}$ are $C_1$-$C_4$alkyl,

If $R_{11}$ and $R_{12}$ together with the C atom to which they are attached form a 5 to 7 membered saturated carbocyclic ring, they together with the C-atom to which they are attached form a cyclopentyl, cyloohexyl or cycloheptyl ring, preferably a cyclohexyl ring, giving rise for example to structures like

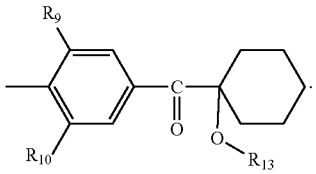

$R_{13}$ for example is hydrogen, $C_1$-$C_4$alkyl, $C_5$-$C_7$cycloalkyl or 2-tetrahydropyranyl;
or $R_{13}$ is hydrogen, $C_1$-$C_4$alkyl, $C_5$-$C_7$cycloalkyl or 2-tetrahydropyranyl;
or $R_{13}$ for example is for hydrogen, $C_1$-$C_4$alkyl or $C_5$-$C_7$cycloalkyl.
or $R_{13}$ is for example hydrogen or, preferably hydrogen.

The preferences for $R'_{13}$ as having one of the meanings as given for $R_{13}$ are as defined above for $R'_{13}$. $R'_{13}$ is for example hydrogen or a group C

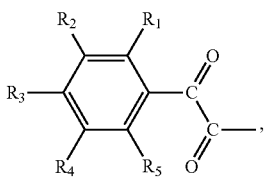

in particular hydrogen.
m is 1 or 2, in particular 1.
If m is 2, this gives rise to dimeric structures of the formula (Ia)

Non-limiting examples of divalent groups $R_3$ (if m is 2) are —O—, S—, —C(=O)—, or —CH$_2$—

In particular interesting are compounds of the formula I, wherein m is 1.

Preferred are compounds of the formula I, wherein m is 1;
$R_1$, $R_2$, $R_4$ and $R_5$ are hydrogen;
$R_3$ has one of the meanings as given above for $R_1$, $R_2$, $R_4$ and $R_5$;

$R_8$ is hydrogen or $C_1$-$C_4$alkyl;
$R_7$ is hydrogen,
$R_8$ is group A or B
X is O, O—CH$_2$— or —O(CHR$_{14}$)—;
n is 0 or 1;
provided that
(i) if n is 0, and X is O, then $R_8$ is a group A;
(ii) if n is other than 0, then X is O and $R_8$ is the group A;
$R_9$ and $R_{10}$ are hydrogen or $C_1$-$C_4$alkyl;
$R_{11}$ and $R_{12}$ are $C_1$-$C_4$alkyl;
$R_{13}$ is hydrogen,
$R_{14}$ is a group A'; and
$R'_{13}$ has one of the meanings as given for $R_{13}$ or is the group C

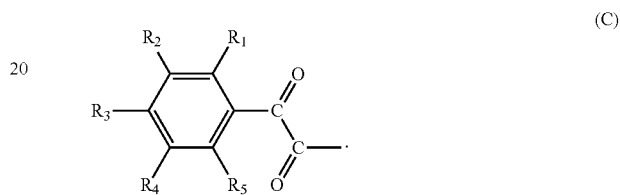

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprise" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

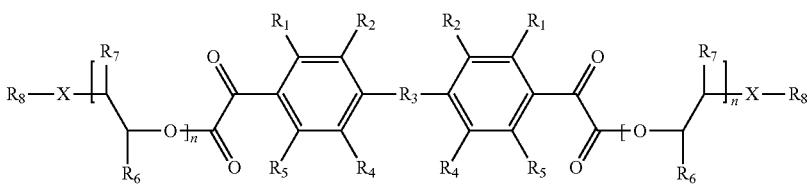

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "ad" and "the" include plural referents unless the context clearly dictates otherwise.

If nothing else is defined, any terms and scientific terminology used herein are intended to have the meanings commonly understood by those of skill in the art to which this invention pertains.

The compounds of the present invention can be made by several methods.

One possibility is the acylation of the OH functionalized α-hydroxyketone (HO-AHK) with suitable derivatives of optionally substituted phenyl glyoxylic acid (PhCOCOY or PhCOCO—O—COCOPh) according

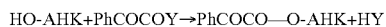

where Y denotes Cl or Br) or

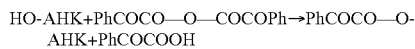

For example, the acylation can be performed with the chloride, bromide (Y) or anhydride of the phenyl glyoxylic acid. Mixed anhydrides of phenyl glyoxylic acid, for example with pivalic acid or methane sulfonic acid, can be also used.

Addition of a suitable inorganic or organic base to neutralize the liberated acid H—Y may facilitate the reaction. Not limiting examples are NaOH, NaHCO$_3$, Na$_2$CO$_3$, K$_2$CO$_3$, Ca(OH)$_2$, triethylamine or pyridine.

From a process point of view it may be advantageous to use a base which forms with the acid HY a liquid salt, so called ionic liquid. Non limiting example of such base is e.g. 1-methylimidazole.

The reaction is performed without solvent or in a suitable solvent. Excess of the amine base can be used as a solvent or for example a mixture of solvents like toluene, ethylacetate, dichloromethane, chlorobenzene, t-butyl-methylether can be used, to name just a few examples. The reaction can be also run in a biphasic system consisting of water and a solvent which is not miscible with water. Addition of a phase-transfer catalyst, for example an ammonium or phosphonium salt may be beneficial in this case.

The reaction temperature is dictated by the reactivity of the employed HO-AHK and phenyl glyoxylic acid derivative, solvent and base and may vary in a broad range, e.g. from −50 to 150° C., typically from 0 to 100° C.

Esterification of the free phenyl glyoxylic acid with the HO-AHK can be also used, an acidic catalyst such as e.g. H$_2$SO$_4$, HCl or p-toluene sulfonic acid will accelerate the reaction. Removal of the reaction water by running the reaction under reduced pressure or with the help of suitable entrainer, for example toluene, benzene or cyclohexane will also speed up the reaction and increase the yield.

The reaction between the free phenyl glyoxylic acid and HO-AHK can also be achieved with the help of suitable dehydrating reagents, for example with carbodiimides such as dicyclohexylcarbodiimide.

Yet another method for preparation of the inventive compounds is transesterification of esters of phenyl glyoxylic acid PhCOCOOR with the HO-AHK derivative according to

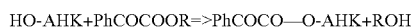

where R denotes for example C$_1$-C$_4$alkyl, e.g. methyl or ethyl.

Diverse esters of phenyl glyoxylic acid PhCOCOOR can be used, for example the methyl or ethylester or diester with diethylene glycol (available under the tradename Irgacure® 754 from BASF). Typically, the transesterification reaction will be catalysed. Variety of transesterification catalysts can be used, non-limiting examples are alcoholates or carboxylates of alkali metals, lithium amide, organotin compounds such as dibutyltin dilaurate, dibutyltin oxide or tin(II) oxalate, zirconium(IV)-, vanadyl-, iron(III)-, copper(II)-, vanadium(III)- or manganese(II)-acetonylacetate, thiamine nitrate, aluminium lactate, zeolites, ion exchangers. Removal of the reaction alcohol ROH by running the reaction under reduced pressure or with the help of suitable entrainer, for example toluene, benzene cyclohexane, octane or decane will also speed up the reaction and increase the yield. Either the HO-AHK derivative or the phenyl glyoxylic acid ester can be used in excess. The excess of the respective reagent can be removed after the reaction, for example by distillation or crystallization. However, it can be also left in the reaction mixture which can be then used as polymerization initiator directly as a "product by process".

Subject of the invention also is a process for the preparation of compounds of the formula I as defined in claim 1, wherein a OH functionalized α-hydroxyketone of the formula III

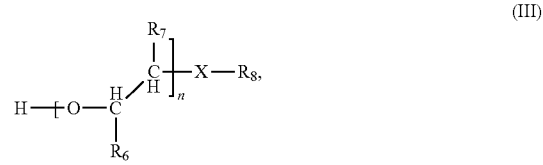

wherein
X, n, R$_6$ and R$_7$ are as defined in claim 1,
is acylated with phenyl glyoxylic acid or a derivative of a phenyl glyoxylic acid of the formula IVa or IVb

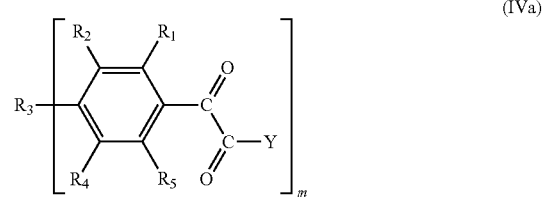

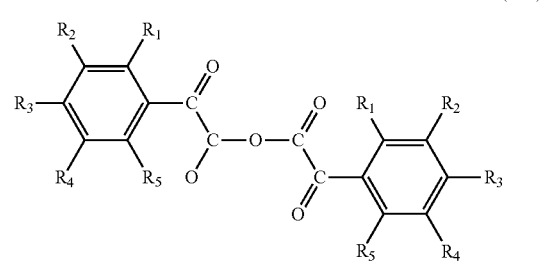

wherein
R$_1$, R$_2$, R$_3$, R$_4$, R$_5$ and m are as defined in claim 1 and
Y is OH, Cl or Br,
optionally in the presence of a base.

In accordance with the invention, the compounds of the formula I can be used as photoinitiators for the photopolymerization of ethylenically unsaturated compounds.

The invention therefore also relates to photopolymerizable compositions comprising (A) at least one ethylenically unsaturated photopolymerizable compound and (B) at least one photoinitiator of the formula I as defined above.

The composition may comprise additionally to the component (B) at least one further photoinitiator (C), and/or further coinitiators (D) and/or other additives.). In other words the composition comprises components (A) and (B) and a component selected from the group consisting of further photoinitiators (C) and other (customary) additives (D).

The unsaturated compounds (A) for example contain one or more olefinic double bonds. They are of low molecular weight (monomeric) or higher molecular weight (oligomeric)

Examples of monomers containing a double bond are (meth)acrylic acid and salts thereof, (meth)acrylic acid esters, e.g. alkyl esters such as methyl, ethyl, 2-chloroethyl, N-dimethylaminoethyl, n-butyl, isobutyl, pentyl, hexyl, cyclohexyl, 2-ethylhexyl, octyl, isobornyl [2-exobornyl] ester, phenyl, benzyl and o-, m- and p-hydroxyphenyl ester, hydroxyalkyl esters, e.g. 2-hydroxyethyl, 2-hydroxypropyl, 4-hydroxybutyl, 3,4-dihydroxybutyl or glycerol [1,2,3-propanetriol] ester, epoxyalkyl esters, e.g. glycidyl, 2,3-epoxybutyl, 3,4-epoxybutyl, 2,3-epoxycyclohexyl, 10,11-epoxyundecyl ester, (meth)acrylamides, N-substituted (meth)acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMAA (N-isobutoxymethylacrylamide), (meth)acrylonitriles, unsaturated acid anhydrides such as itaconic anhydride, maleic anhydride, 2,3-dimethylmaleic anhydride, 2-chloromaleic anhydride, unsaturated esters such as maleic acid esters, phthalic acid esters, itaconic acid esters [methylenesuccinic acid esters], styrenes such as methylstyrene, chloromethylstyrene and o-, m- and phydroxystyrene, divinylbenzene, vinyl ethers such as isobutyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether, vinyl and allyl esters such as vinyl acetate, vinyl acrylate, vinyl chloroacetate, vinyl butyrate and vinyl benzoate, divinyl succinate, diallyl phthalate, triallyl phosphate, vinyl chloride and vinylidene chloride, isocyanurates such as triallyl isocyanurate and tris(2-acryloylethyl) isocyanurate. N-vinylheterocyclic compounds such as N-vinylpyrrolidones or substituted N-vinylpyrrolidones, N-vinylcaprolactam or substituted N-vinylcaprolactams, N-vinylcarbazole, N-vinylpyridine.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Further examples of suitable esters are:
diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having molecular weights of from 200 to 1500, or mixtures thereof.

Frequently also used are acrylic acid esters of alkoxylated alcohols, e.g. glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, unsaturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxyphenyl)propane, and also novolaks and resols. Examples of polyepoxides are those based on the mentioned polyols, especially aromatic polyols and epichlorohydrin. Also suitable as polyols are polymers and copolymers that contain hydroxyl groups in the polymer chain or in side groups such as, for example, polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of polyurethanes are those composed of saturated diisocyanates and unsaturated diols or unsaturated diisocyanates and saturated diols.

Preference is given to (meth)acrylated epoxy esters, (meth)acrylated polyesters, polyesters carrying vinyl groups, (meth)acrylated polyurethanes, (meth)acrylated polyethers and polyols, in particular to the acrylated corresponding components.

Suitable components (A) are also acrylates which have been modified by reaction with primary or secondary amines, as described, for example, in U.S. Pat. No. 3,844,916, in EP280222, in U.S. Pat. No. 5,482,649 or in U.S. Pat. No. 5,734,002. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOMER 5275 from Rahn.

Some acrylate binders especially designed for low extractables and odour applications can also be used in the formulation. Such resins are commercially available for example under the tradename Ebecryl LEO resins.

Furthermore, cationically UV-curable compositions may be used as part of component (A) for hybrid cationic/radical UV-curing. Such systems typically comprise aliphatic and/or aromatic epoxides, at least one polyol or polyvinyl polyol or oxetane and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555. In addition, ethylenically unsaturated compounds may be added to the said cationically UV-curable compositions.

It is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (A), at least one ethylenically unsaturated photopolymerisable compound dissolved or emulsified in water. Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

Used are, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP012339. Mixtures of those prepolymers may also be used. Also suitable are, for example, the polymerisable prepolymers described in EP033896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth) acrylic acid alkyl ester polymerisation products are described in EPO41125; suitable water-dispersible, radiation-curable prepolymers obtained from urethane acrylates are to be found in, for example, DE2936039.

The photopolymerisable compounds (A) are used singly or in any desired mixture.

Component (A) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000-2 000 000, preferably 10 000-1 000 000. Examples area homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam und poly(hexamethylene adipamide), polyesters, e.g. poly(ethylene glycol terephthalate) and poly(hexamethylene glycol succinate).

The unsaturated compounds may also be used in admixture with non-photopolymerisable film-forming components. The latter are, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1,3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (A) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991.

The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 describe maleimide-modified binders. Maleimide-modified binders of that kind may likewise be present in the photocurable composition of the present invention.

Examples of binders are:
1. surface-coatings based on cold- or hot-crosslinkable alkyd, acrylate, polyester, epoxy or melamine resins or mixtures of such resins, optionally with the addition of a curing catalyst;
2. two-component polyurethane surface-coating compositions based on hydroxyl-group-containing acrylate, polyester or polyether resins and aliphatic or aromatic isocyanates, isocyanurates or polyisocyanates;
3. two-component polyurethane surface-coating compositions based on thiol-group-containing acrylate, polyester or polyether resins and aliphatic or aromatic isocyanates, isocyanurates or polyisocyanates;
4. single-component polyurethane surface-coating compositions based on blocked isocyanates, isocyanurates or polyisocyanates, which are unblocked during stoving; optionally, the addition of melamine resins is also possible;
5. single-component polyurethane surface-coating compositions based on aliphatic or aromatic urethanes or polyurethanes and hydroxyl-group-containing acrylate, polyester or polyether resins;
6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides and polyepoxides;
12. two-component surface-coating compositions based on (poly)oxazolines and anhydride-group-containing acrylate resins or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically cross-linking acrylate resins, in combination with etherified melamine resins;
15. surface-coating systems, especially clearcoats, based on malonate-blocked isocyanates with melamine resins (e.g. hexamethoxymethyl melamine) as crosslinkers (acid-catalysed);
16. UV-curable systems based on oligomeric urethane acrylates and/or acylate acrylates, optionally with the addition of other oligomers or monomers;
17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of coating or ink technology will be familiar with such measures.

The photopolymerizable composition of the invention for example additionally comprises a binder polymer (E), in particular a copolymer of methacrylate and methacrylic acid.

In addition to the photoinitiator, the photopolymerisable mixtures may comprise various additives (D). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)decanedioate or polyalkyl-piperidin-N-oxyl radicals, 3-aryl-benzofuran-2-one and derivatives thereof, e.g. 5,7-ditert-butyl-3-phenyl-3H-benzofuran-2-one (as described in, for example, WO01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS). Such compounds are widely known to the person skilled in the art.

Examples of such UV absorbers and light stabilisers are disclosed in WO04/074328, page 12, line 9 to page 14, line 23, said disclosure hereby is incorporated by reference.

Further, additives that are customary in the art such as, for example, antistatics, flow improvers and adhesion promoters may be used.

Further additives which may be included in radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In accordance with the invention, if the formulation comprises binder, thermal drying or curing catalysts may additionally be added to the formulation as additional additives (D). Possible drying catalysts, or thermal curing catalysts, are, for example, organic metal compounds, amines or/and phosphines. Organic metal compounds are, for example, metal carboxylates, especially those of the metals Pb, Mn, Hf, Ce, Co, Zn, Zr, Bi or Cu, or metal chelates, especially those of the metals Hf, Al, Bi, Zn, Ti or Zr, or organometal compounds, such as e.g. organotin compounds. Examples of metal carboxylates are the stearates of Pb, Mn, Bi or Zn, the octoates of Co, Zn, Bi or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyl-trifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenylphosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic.

Such catalysts are used in concentrations customary in the art and known to the skilled person.

In order to accelerate photopolymerisation, amines may be added as further additives (D), especially tertiary amines, e.g. tributylamine, triethanolamine, p-dimethylaminobenzoic acid ethyl ester. Michler's ketone, N-methyl-diethanolamine, N-dimethylethanolamine, N-ethylmorpholine, N-methylmorpholine, diazabicyclooctane (triethylenediamine), 18-diazabicyclo[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone or thioxanthone type. Amines that are suitable as oxygen capture agents are, for example. N,N-dialkylanilines as described in EP339841 Further accelerators, coinitiators and auto-oxidisers are thiols, thioethers, disulfides and phosphines as described in, for example, EP438123 and GB2180358.

It is also possible for chain transfer reagents customary in the art to be added to the compositions according to the invention. Examples are mercaptans, amines and benzothiazole.

Photopolymerisation can also be accelerated by addition, as further additives (D), of photosensitisers, which shift or broaden the spectral sensitivity. These include especially aromatic carbonyl compounds such as, for example, benzophenone derivatives, thioxanthone derivatives, including especially diethyl-, isopropyl-thioxanthone, anthraquinone derivatives and 3-acylcoumarin derivatives, terphenyls, styryl ketones, and 3-(aroylmethylene)thiazolines, camphorquinone and also eosin, rhodamine and erythrosine dyes.

The amines mentioned above, for example, may also be regarded as photosensitisers. Examples of suitable sensitizer compounds (D) are disclosed in WO06/008251, page 36, line 30 to page 38, line 8, the disclosure of which is hereby incorporated by reference. Subject of the invention therefore also is a photopolymerizable composition as described above, as further additive (D) comprising a photosensitizer.

The curing process, especially of pigmented (e.g. pigmented with titanium dioxide) compositions, can also be assisted by adding an additional additive (D) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP245639.

Further customary additives (D) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5,013,768.

The formulations may also comprise dyes and/or white or coloured pigments [as further additive (D)]. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use of the photopolymerizable composition and the properties desired in that field.

Subject of the invention also is a photopolymerizable composition as described above as further additive (D) comprising a pigment, a dye, a mixture of pigments, a mixture of dyes or a mixture of one or more pigments with one or more dyes.

Subject of the invention also is a photopolymerizable composition as described above as further additive (D) comprising a dispersant or a mixture of dispersants.

The additives (D) described hereinbefore are customary in the art and are accordingly used in amounts customary in the art.

In certain cases it may be of advantage to use mixtures of two or more of the novel photoinitiators. It is of course also possible to use mixtures with known photoinitiators (C), for example mixtures with camphor quinone; benzophenone, benzophenone derivatives, such as 2,4,6-trimethylbenzophenone, 2-methylbenzophenone, 3-methylbenzophehone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxybenzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone,

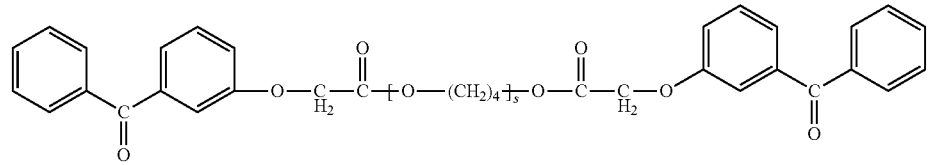

with s=1-20, a mixture of

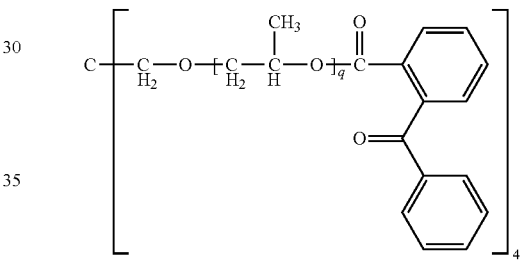

with q about 2 and

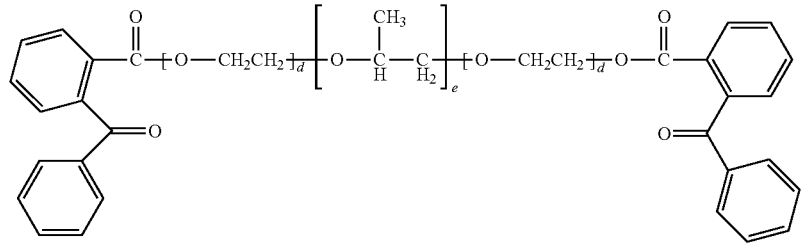

wherein the sum of d and e is about 14, where d is greater than e,

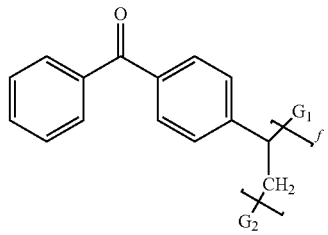

with f=about 14;

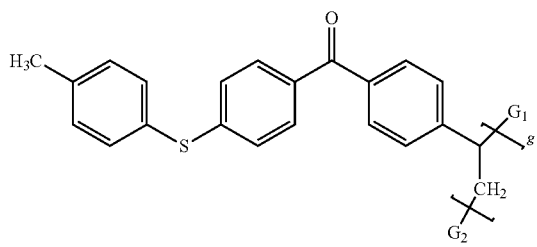

with g=about 12;

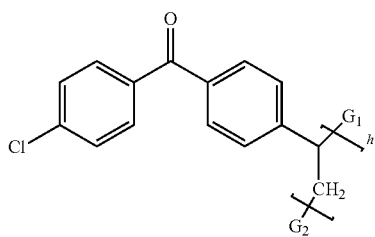

with h=about 13, and any blends or admixtures of the above mentioned compounds; thioxanthones, thioxanthone derivatives, polymeric thioxanthones as for example OMNIPOL TX; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropyl-benzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminoazoyl)-1-benzyl-1-pane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]ethyl ester; ketosulfones, ESACURE KIP 1001 M; oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethylbenzoyl)diphenylphosphine oxide, ethyl (2,4,6 trimethylbenzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl[1,3,5]triazine, hexaarylbisimidazole/coinitiators systems, e.g. ortho-chlorohexaphenyl-bisimidazole combined with 2-mercaptoben-zthiazole, ferrocenium compounds, or titanocenes, e.g. bis(cyclo)-bis(2,6-difluoro-3-pyrryl-phenyl)titanium. Further, borate compounds can be used as coinitiators. As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP provided by Fratelli Lamberti, or oligomeric alpha amino ketones may be employed as well.

Mixtures of the compounds of the invention with known photoinitiators (C) are especially attractive, if the mixture of the compound of the invention with the photoinitiator(s) is a liquid, since such liquids can easily be handled and incorporated into the formulation. Especially attractive are mixtures where either the compound of the invention or the photoinitiator (C) are liquids, since this allows the compounds to be mixed over a large ratio. Most preferred are mixtures where both the compound of the invention and the photoinitiator (C) are liquids, since this allows the components to mixed in any ratio.

Many of said additional photoinitiators (C) are commercially available, for example under the tradenames Darocur® and Irgacure® from BASF SE.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17-25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-isopropylbenzene)($\eta^5$-cyclopentadienyl)iron (II) hexafluorophosphate or oxime sulfonates. Suitable sulfonium salts are obtainable, for example, under the trade names ®Cyracure UVI-6990, ®Cyracure UVI-6974 (Union Carbide), ®Degacure KI 85 (Degussa), SP-55, SP-150, SP-170 (Asahi Denka), GE UVE 1014 (General Electric), SarCat® KI-85 (=triarylsulfonium hexafluorophosphate; Sartomer), SarCat® CD 1010 (=mixed triarylsulfonium hexafluoroantimonate; Sartomer); SarCat® CD 1011(=mixed triarylsulfonium hexafluorophosphate; Sartomer).

Suitable iodonium salts are e.g. tolylcumyliodonium tetrakis(pentafluorophenyl)borate, 4-[(2-hydroxy-tetradecyloxy)phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate, 4-octyloxyphenylphenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable.

Suitable examples of oximesulfonates are α-(octylsulfonyloxyimino)-4-methoxybenzylcyanide, 2-methyl-α-[5-[4-[[methyl-sulfonyl]oxy]imino]-2(5H)-thienylidene]-benzeneacetonitrile, 2-methyl-α-[5-[4-[[(n-propyl)sulfonyl]oxy]

imino]-2(5H)-thienylidene]-benzeneacetonitrile, 2-methyl-α-[5-[4-[[(camphoryl)sulfonyl]oxy]imino]-2(5H)-thienylidene]-benzeneacetonitrile, 2-methyl-α-[5-[4-[[(4-methylphenyl)sulfonyl]oxy]imino]-2(5H)-thienylidene]-benzeneacetonitrile, 2-methyl-α-[5-[4-[[(n-octyl)sulfonyl]oxy]imino]-2(5H)-thienylidene]-benzeneacetonitrile, 2-methyl-α-[5-[[[4-[[(4-methylphenyl)sulfonyl]oxy]phenyl]-sulfonyl]oxy]imino]-2(5H)-thienylidene]-benzeneacetonitrile, 1,1'-[1,3-propanediylbis(oxy-4,1-phenylene)]bis[2,2,2-trifluoro-bis[O-(trifluoromethylsulfonyl)oxime]-ethanone, 1,1'-[1,3-propanediylbis(oxy-4,1-phenylene)]bis[2,2,2-trifluoro-bis[O-(propylsulfonyl)oxime]-ethanone, 1,1'-[1,3-propanediylbis(oxy-4,1-phenylene)]bis[2,2,2-trifluoro-bis[O-((4-methylphenyl)sulfonyl)oxime]-ethanone, 2-[2,2,3,3,4,4,5,5,6,6,7,7-dodecafluoro-1-(nonafluorobutylsulfonyloxyimino)-heptyl]-fluorene, 2-[2,2,3,3,4,4,4-heptafluoro-1-(nonafluorobutylsulfonyloxyimino)-butyl]-fluorene, 2-[2,2,3,3,4,4,5,5,6,6,7,7-dodecafluoro-1-(nonafluorobutylsulfonyloxyimino)-heptyl]-9-thia-fluorene.

This list is not meant to be conclusive for additional photoinitiator compounds to be used in combination with the novel compounds of the inventions.

Subject of the invention accordingly also is a photopolymerizable composition as described above, wherein the additional photoinitiator (C) is selected from the group consisting of alpha-hydroxy ketones, benzophenone, substituted benzophenone compounds, thioxanthones, benzildimethylketal, phenylglyoxylate compounds, mono-, bis-, tris acylphosphineoxides and alpha-amino ketone compounds.

Preferably the additional photoinitiator (C) is selected from the group consisting of benzophenone, 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone, benzildimethylketal, acetophenone, 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]phenyl}-2-methyl-propan-1-one; 2-hydroxy-1-{4-[4-(2-hydroxy-2-methyl-propionyl)phenoxy]-phenyl}-2-methyl-propan-1-one, (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminobenzoyl)-1-benzyl-1-dimethylaminopropane), (3,4-dimethoxybenzoyl)-1-benzyl-1-dimethylaminopropane, methyl α-oxo benzeneacetate, oxo-phenyl-acetic acid 2-(2-hydroxy-ethoxy)-ethyl ester and oxo-phenyl-acetic acid 1-methyl-2-[2-(2-oxo-2-phenyl-acetoxy)propoxy]-ethyl ester, Esacure® KIP150, Esacure® ONE and Esacure® KIP160.

Further preferred examples of additional photoinitiators (C) are selected from the group consisting of 2-hydroxy-2-methyl-1-phenyl-propanone, 1-hydroxy-cyclohexyl-phenyl-ketone, 2-hydroxy-1-{4-[4-(2-hydroxy-2-methyl-propionyl)-benzyl]-phenyl}-2-methyl-propan-1-one, Esacure KIP® 150, Esacure® ONE and Esacure® KIP160, methyl α-oxo benzeneacetate, oxo-phenyl-acetic acid 2-(2-hydroxy-ethoxy)-ethyl ester and oxo-phenylacetic acid 1-methyl-2-[2-(2-oxo-2-phenyl-acetoxy)-propoxy]-ethyl ester.

In particular preferred additional photoinitiators (C) are selected from the group consisting of 2-hydroxy-2-methyl-1-phenyl-propanone, 1-hydroxy-cyclohexyl-phenyl-ketone and 2-hydroxy-1-{4-[4-(2-hydroxy-2-methyl-propionyl)-benzyl]-phenyl}-2-methyl-propan-1-one.

The photopolymerizable compositions generally comprise 0.05 to 15% by weight, preferably 0.1 to 10% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

The compositions according to the invention can be used for various purposes, for example in overprint coatings, as printing ink, e.g. screen printing ink, ink for offset- or flexo printing, gravure printing, inkjet ink (lithography or continuous or dropwise ink-jet printing on for example material pretreated in accordance with the process as disclosed in WO 03/064061 using generally known formulations), ink for sheet-fed printing, electrophotography ink, intaglio ink, for example in publishing, packaging or shipping, in logistics, in advertising, in security printing or in the field of office equipment, as clearcoats, white coats or coloured- (pigmented or dyed) coats, e.g. for wood or metal, as powder coatings, as paints, inter alia for paper, wood, metal or plastics, as daylight-curable paints for marking structures and roads, paints for buildings, constructions, vehicles, aircraft, wind energy plant, etc., for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical equipment, auxiliaries, aids or implants. The compositions can also be used for the preparation of gels having thermotropic properties. Such gels are described in, for example, DE19700064 and EP678534.

The compositions according to the invention can also be used in dry paint film, as for example described in Paint&Coatings Industry, April 1997, 72 or Plastics World, vol. 54, no. 7, p 48(5).

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions act as a crosslinking agent which renders the film insoluble. The monounsaturated monomer functions act as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The photoinitiators according to the invention may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth)acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator according to the invention. The powder coatings may also comprise binders, as described in, for example, DE4228514 and EP636669. The powder coating formulations described in EP636669 comprise, for example, 1) an unsaturated resin from the group of (semi-)crystalline or amorphous unsaturated polyesters, unsaturated polyacrylates or mixtures thereof with unsaturated polyesters, with special preference being given to those derived from maleic acid or fumaric acid; 2) an oligomeric or polymeric crosslinking agent containing vinyl ether-, vinyl ester- or (meth)acrylate-functional groups, with special preference being given to vinyl ether oligomers, for example divinyl ether-functionalised urethanes; 3) the photoinitiator.

The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. in contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The photoinitiator according to the invention may also be used in the form of an aqueous, for example 0.5-5%, preferably 0.5-2%, dispersion in polymer dispersions, for example in aqueous polyurethane dispersions, so-called PUDs.

A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiators, the powder coating formulations may also include UV absorbers. To appropriate examples is referred above.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of image-wise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by printing methods such as flexography printing, lithography printing, inkjet, screen printing, spin-coating, immersion, roller application, reverse-roll application, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500. The amount applied (layer thickness) and the nature of the substrate (layer support) are dependent on the desired field of use.

The quantity applied (coat thickness) and the nature of the substrate (layer support) are dependent on the desired field of application. The range of coat thicknesses generally comprises values from about 0.01 µm to more than 100 µm, for example 20 mm or 0.02 to 10 cm, preferably 0.5 to 100 µm.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electrophotographic inks, sheetfed inks, overprint varnishes or primers.

As already mentioned above, the photoinitiator is suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parks are subsequently washed out using an appropriate solvent or aqueous solutions.

Printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 5 to 5000 mPa·s, for example from 10 to 2000 mPa·s, for liquid printing inks. For paste-form printing inks, the values range, for example, from 1 to 200 Pa·s, preferably from 5 to 100 Pa·s. The person skilled in the art will be familiar with the ingredients and compositions of printing inks.

Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 20% by weight, based on the total weight of the printing ink.

The printing inks can be used, for example, for intaglio printing, gravure printing, flexographic printing, screen printing, offset printing, lithography or continuous or drop-wise inkjet printing using generally known formulations, for example in publishing, packaging or shipping, in logistics, in advertising, in security printing or in the field of office equipment. Suitable printing inks are both solvent-based printing inks and water-based printing inks. Of interest are, for example, printing inks based on aqueous acrylate. Such inks are to be understood as including polymers or copolymers that are obtained by polymerisation of at least one monomer containing a group

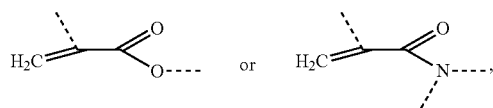

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per se.

The printing inks may, for example, also comprise alkyd systems that dry. oxidatively.

The printing inks are dried in a known manner customary in the art, optionally with heating of the coating.

A suitable aqueous printing ink composition comprises, for example, a pigment or a combination of pigments, a dispersant and a binder.

Subject of the invention therefore also is a photopolymerizable composition as described above as further additive (D) comprising a dispersant or a mixture of dispersants. Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids. Such dispersants are known and are described, for example, in U.S. Pat. No. 5,186,846 and DE19727767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol. It is also possible, for example, to use polymeric acids which act both as dispersants and as binders.

Examples of suitable binder components that may be mentioned include (meth)-acrylate-group-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP704469, EP012339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≤1% by weight, based on the weight of the preparation.

Printing inks include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from BASF SE.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_5$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. ∈-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed.

Suitable substrates are, for example, textile fibre materials, paper, plastics or aluminium foils. Suitable recording systems are e.g. commercially available ink-jet printers.

Preference is given to printing processes in which aqueous printing inks are used. Preferred in ink-jet ink formulations comprise (meth)acrylated epoxy esters; (meth)acrylated polyesters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. No. 3,844,916, EP280222, U.S. Pat. No. 5,482,649 or U.S. Pat. No. 5,734,002. Such amine-modified acrylates are also termed aminoacrylates. Examples are already given hereinbefore. It is known that in the presence of aminoacrylates UV-curable systems show an increased curing performance. They are useful to overcome the oxygen inhibition typically observed for radical induced polymerization reactions, especially for low viscous systems like UV-curable inkjet.

It will be clear that mixtures of all these cited monomers, prepolymers, polymers and oligomers can be used in the ink compositions comprising the photoinitiator according to the present invention.

The amount of the photopolymerizable monomer, oligomer or prepolymer in this connection is for example 10 to 990 wt %, preferably 10 to 90 wt %.

The inks comprising the photoinitiator of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available. Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above.

Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the photoinitiator as described above.

Ink jet inks for example contain a colorant. A wide variety of organic and inorganic dyes and pigments, alone or in combination may be selected for use in ink jet ink compositions; the person skilled in the art is familiar with the appropriate choice. The pigment particles should be sufficiently small (0.005 to 15 μm) to permit free flow of the ink at the ejecting nozzles. The pigment particles should preferably be 0.005 to 1 μm.

Very fine dispersions of pigments and their preparation are disclosed in e.g. U.S. Pat. No. 5,538,548.

The inks preferably comprise a total content of colorant of 1 to 35% by weight, in particular 1 to 30% by weight, and preferably 1 to 20% by weight, based on the total weight of ink. A limit of 2% by weight, in particular 2.5% by weight, and preferably 3% by weight, is preferred here as the lower limit.

Suitable colorants are for example pure pigment powders such as Cyan IRGALITE® Blue GLO (BASF SE) or pigment preparations such as MICROLITH-pigment preparations.

Ink jet inks may include a variety of further additives such as for example surfactants, biocides, buffering agents, anti-mould agents, pH adjustment agents, electric conductivity adjustment agents, chelating agents, anti-rusting agents, polymerisation inhibitors, light stabilizers, and the like. Such additives may be included in the ink jet inks in any effective amount, as desired.

A preferred field of use comprises overprint coatings and also pigmented thin coatings (layer thickness<20 μm), for example printing inks that are used in printing methods such as, for example, flexographic printing, offset printing, screen printing, intaglio printing, gravure printing, letterpress printing, tampon printing and inkjet printing.

Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

Subject of the invention therefore also is a photopolymerizable composition as described above, which is a printing ink, in particular an offset printing ink.

The photoinitiators of the present invention are also suitable for use in UV-curable adhesives; e.g. in the preparation of pressure-sensitive adhesives, laminating adhesives, hotmelt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers. The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The photoinitiators according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

A further field of use comprises compositions that are suitable for the coating of glass fibres, both for the inner and also for the middle and outer layers. The coated glass fibres may also be gathered into bundles giving a further coating. Such coating layers comprise UV-curable oligomers, UV-curable monomers and also at least one photoinitiator and additives.

Any UV-curable oligomer is suitable for the coating of glass fibres.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

Further fields of use of photocuring are wood coatings, for example the application of a UV curable coating to wood substrates used e.g. for parquet flooring, furniture, kitchen cabinets or printed decor laminates, HDF or MDF substrates The novel photoinitiators further find application in formulations for negative resists, having a very high sensitivity to light and being able to be developed in an aqueous alkaline medium without swelling. They are suitable as photoresists for electronics (electroplating resist, etch resist, solder resist), the production of printing plates, such as offset printing plates or flexo printing plates, for the production of printing forms for relief printing, plano-graphic printing, rotogravure or of screen printing forms, for the production of relief copies, for example for the production of texts in braille, for the production of stamps, for use in chemical milling or as a microresist in the production of integrated circuits. The possible layer supports, and the processing conditions of the coating substrates, are just as varied. The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 μm to 10 μm, while for printed circuits it is from 1.0 μm to about 100 μm.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37. Following the imagewise exposure of the material and prior to development, it may be advantageous to carry out thermal treatment for a short time. In this case only the exposed sections are thermally cured. The temperatures employed are generally 50-150° C., preferably 80-130° C.; the period of thermal treatment is in general between 0.25 and 10 minutes. Conjugated polymers, like e.g. polyanilines can be converted from a semiconductive to a conductive state by means of proton doping. The oxime-sulfonates of the present invention can also be used to imagewise irradiate compositions comprising such conjugated polymers in order to form conducting structures (exposed areas) embedded in insulating material (non-exposed areas). Such materials can for example be used as wiring and connecting parts for the production of electric and electronic devices.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation. After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset and flexo inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueos solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag BerlinHeidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate coloration produces visible images. Where the support is a metallized layer, the metal can, following exposure and development, be etched away at the unexposed areas or reinforced by electroplating. In this way it is possible to produce electronic circuits and photoresists.

The photopolymerizable compositions further can be used for the production of functional glass, as is for example described in JP 10 287450 A.

The photocurable compositions of the invention can further be used for curing of charged monomers, e.g. acrylates with $NH_4Cl$-groups etc. usw. Such compositions are for example employed for preparing polyelektrolytes or corresponding copolymers.

The photoinitiators of the formula I are in particular suited for coatings on wood, they only emit low odord and don't emit benzaldehyde.

The invention also provides a process for the photopolymerization of monomeric, oligomeric or polymeric compounds containing at least one ethylenically unsaturated double bond, which comprises adding to the abovementioned compounds at least one photoinitiator or photoinitiator mixture as described above and irradiating the resulting composition with electromagnetic radiation, for example light of the wavelength 200 to 600 nm or with particulate radiation, such as for example electron beam or X-ray; as well as the use of a photoinitiator or photoinitiator mixture as defined above for the photopolymerization of monomeric, oligomeric or polymeric compounds containing at least one ethylenically unsaturated double bond.

The invention additionally provides the use of compositions as described above for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules; as well as a process for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

The invention further provides a coated substrate which is coated on at least one surface with a composition as described above, and a polymerized or crosslinked composition obtained by curing a polymerizable composition as described above.

The photosensitivity of the compositions according to the invention usually extends from approximately 150 nm into the IR range. For example from about 150 nm through the UV region and into the infrared region (about 20,000 nm, in particular 1200 nm), especially from 190 nm to 650 nm (depending on the photoinitiator moiety, optionally in combination with a sensitizer as described hereinbefore) and therefore spans a wide range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used. Alternatively, the actinic radiation is provided by light emitting diodes (LED) or organic light emitting diodes (OLED), e.g. UV light emitting diodes (UV-LED). Said LEDs allow instant on and off switching of the radiation source. Further, UV-LEDs generally have a narrow wavelength distribution and offer the possibility to customize the peak wavelength and also provide an efficient conversion of electric energy to UV radiation.

As already mentioned, curing according to the invention can be carried out solely by irradiation with electromagnetic radiation. Depending on the composition of the formulation to be cured, however, thermal curing before, during or after the irradiation is advantageous. As mentioned above, depending on the light source used it is advantageous in many cases to employ a sensitizer, as described above, whose absorption spectrum coincides as closely as possible to the emission spectrum of the radiation source.

Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

EXAMPLE 1

2-[4-(2-Hydroxy-2-methyl-propanoyl)phenoxy]ethyl 2-oxo-2-phenyl-acetate

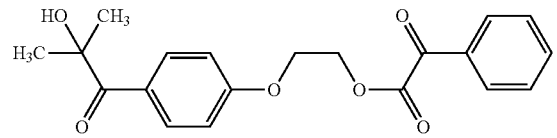 [SMILES: CC(C)(O)C(=O)c1ccc(OCCOC(=O)C(=O)c2ccccc2)cc1]

Acylation of α-hydroxyketone with chloride of phenyl glyoxylic acid. 2-Hydroxy-1-[4-(2-hydroxyethoxy)phenyl]-2-methyl-propan-1-one (Irgacure® 2959, BASF) (3.36 g, 15 mmol) and 4-dimethylaminopyridine (0.1 g) are dissolved in 30 ml of dry pyridine. To this solution is added at 5-10° C. the solution of 2-oxo-2-phenyl-acetyl chloride (2.48 g, 15 mmol) in 30 ml dichloromethane and the resulting mixture is stirred for 1 h at room temperature. It is then diluted with 300 ml of water, and the organic layer is separated. The aqueous phase is extracted with 50 ml of dichloromethane. The combined organic phases are washed with 3×50 ml 2M-HCl and 30 ml 1M-NaHCO$_3$, then dried over MgSO$_4$ and evaporated. The residue is chromatographed on 130 g silica gel with hexane-ethyl acetate to afford 4.08 g of the title compound as thick oil solidifying on standing. Recrystallization from hexane-dichloromethane affords the analytically pure sample as white crystals, mp. 52-54° C.

$^1$H-NMR (CDCl$_3$, 400 MHz, δ ppm): 8.08 (d, 2H), 8.04 (d, 2H), 7.68 (t, 1H), 7.54-7.50 (m, 2H), 6.98 (d, 2H), 4.81-4.79 (m, 2H, CH$_2$), 4.42-4.40 (m, 2H, CH$_2$), 4.20 (s, 1H, OH), 1.63 (s, 6H, 2×CH$_3$).

$^{13}$C-NMR (CDCl$_3$, 100.62 MHz, δ ppm): 202.59, 185.80, 163.51, 161.92, 135.12, 132.46, 132.26, 130.05, 128.96, 126.68, 114.17, 76.00, 65.56, 63.76, 28.63.

EXAMPLE 2

Bis[4-(2-hydroxy-2-methyl-propanoyl)phenyl]
methyl 2-oxo-2-phenyl-acetate

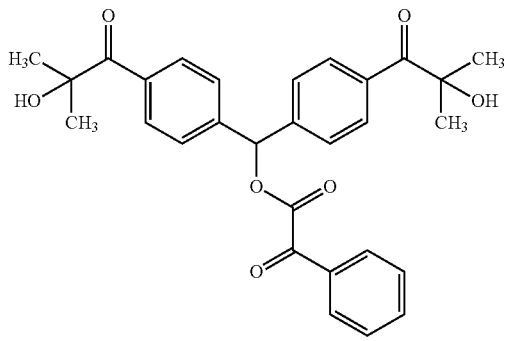 [SMILES: CC(C)(O)C(=O)c1ccc(C(OC(=O)C(=O)c2ccccc2)c2ccc(C(=O)C(C)(C)O)cc2)cc1]

A solution of 2-oxo-2-phenyl-acetyl chloride (12 g, 71 mmol), and 1,1'-[(hydroxymethylene)di-4,1-phenylene]bis[2-hydroxy-2-methyl-1-propanone, (21 g, 59 mmol; prepared according to example 6 of patent application WO2004/099262) in 40 ml tetrahydrofuran is cooled to 0° C. in an ice bath. Triethylamine (9 g, 89 mmol) is added dropwise over 45 min under stirring at 0° C. and 5° C. After 1.5 h, the temperature is allowed to rise to 25° C. overnight. The reaction mixture is poured onto iced water, extracted with ethyl acetate; the organic phases are washed with water to pH 6 and rotary evaporated. The residue is chromatographed on silicagel with dichloromethane:ethyl acetate 9:1 to give two main products. The more polar is compound 2, 14.0 g (49%), obtained as a yellow, viscous oil.

$^1$H-NMR (CDCl$_3$, 400 MHz, δ ppm): 8.06 (d, 4H), 7.95 (d, 2H), 7.66 (t, 1H), 7.48-7.53 (m, 6H), 7.18 (s, 1H), 3.88 (bs, 2 OH), 1.61 (s, 12H).

EXAMPLE 3

[[4-(2-Hydroxy-2-methyl-propanoyl)phenyl]-[4-[2-methyl-2-(2-oxo-2-phenyl-acetyl)oxy-propanoyl]phenyl]methyl] 2-oxo-2-phenyl-acetate

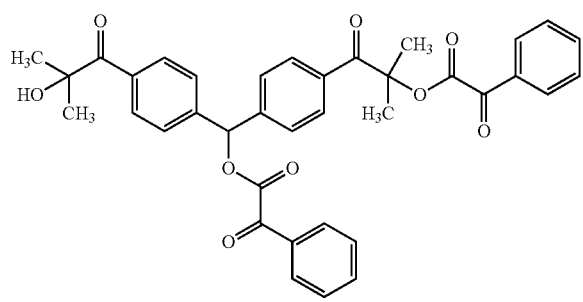 [SMILES: CC(C)(O)C(=O)c1ccc(C(OC(=O)C(=O)c2ccccc2)c2ccc(C(=O)C(C)(C)OC(=O)C(=O)c3ccccc3)cc2)cc1]

This compound is isolated by column chromatography as the less polar product after the experiment of example 2. Yellow viscous oil, 9.0 g (24%).

$^1$H-NMR (CDCl$_3$, 400 MHz, δ ppm): 8.13 (d, 2H), 8.07 (d, 2H), 7.94 (d, 2H), 7.64-7.70 (m, 3H), 7.47-7.58 (m, 7H), 7.36 (t, 2H), 7.17 (s, 1H), 3.86 (s, 1 OH), 1.89 (s, 6H), 1.63 (s, 6H).

EXAMPLE 4

[4-(2-hydroxy-2-methyl-propanoyl)phenyl]methyl
2-oxo-2-phenyl-acetate

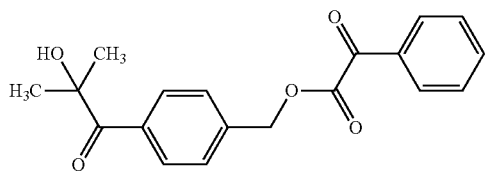 [SMILES: CC(C)(O)C(=O)c1ccc(COC(=O)C(=O)c2ccccc2)cc1]

The product of example 4 is prepared from 2-hydroxy-1-[4-(hydroxymethyl)phenyl]-2-methyl-1-propanone, (obtained according to EP 1763499) by reaction with 2-oxo-2-phenyl-acetyl chloride as described in Example 1. Yellow oil after chromatography.

$^1$H-NMR (CDCl3, 300 MHz, δ ppm): 8.10-7.40 (m, 9ArH), 5.18 (s, 2H, CH$_2$), 4.02 (s, 1H, OH), 1.61 (s, 6H, 2×CH$_3$).

EXAMPLE 5

[3-(2-hydroxy-2-methyl-propanoyl)phenyl]methyl
2-oxo-2-phenyl-acetate

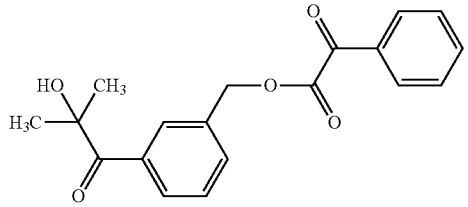 [SMILES: CC(C)(O)C(=O)c1cccc(COC(=O)C(=O)c2ccccc2)c1]

The title compound is prepared in analogy to Example 4 from 2-hydroxy-1-[3-(hydroxymethyl)phenyl]-2-methyl-propan-1-one (prepared as described by Zhang, Yongbo; Wang, Yanchao; Wang, Yapeng; Song, Huaihai; Wang, Zhigang, in WO 2012062041A1, CAN 156:638512, AN 2012:705188) and 2-oxo-2-phenyl-acetyl chloride. Slightly yellow oil, $^1$H-NMR (CDCl$_3$, 400 MHz, δ ppm): 8.10-7.40 (m, 9 ArH), 5.10 (s, 2H, CH$_2$), 4.0 (s, 1H, OH), 1.63 (s, 6H, 2×CH$_3$).

EXAMPLE 6

2-[4-(2-hydroxy-2-methyl-propanoyl)-2,6-dimethyl-phenoxy]ethyl 2-oxo-2-phenyl-acetate

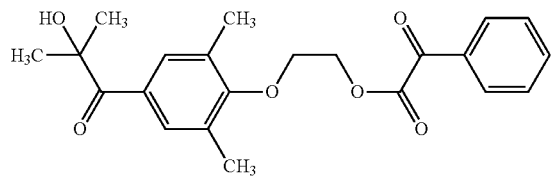 [SMILES: Cc1cc(C(=O)C(C)(C)O)cc(C)c1OCCOC(=O)C(=O)c1ccccc1]

The title compound is prepared in analogy to Example 1 from 2-hydroxy-1-[4-(2-hydroxyethoxy)-3,5-dimethylphenyl]-2-methyl-1-propanone (prepared as described by Nakamura, Masaki, JP 2009143972A, CAN 151:111890, AN 2009:790996) and 2-oxo-2-phenyl-acetyl chloride. Slightly yellow oil,
$^1$H-NMR (CDCl$_3$, 400 MHz, δ ppm): 8.10-7.40 (m, 7 ArH), 4.7 (m, 2H, CH$_2$), 4.3 (m, 2H, CH$_2$), 4.1 (s, 1H, OH), 2.4 (s, 2×CH$_3$), 1.63 (s, 6H, 2×CH$_3$).

EXAMPLE 7

[2-[4-(2-hydroxy-2-methyl-propanoyl)phenoxy]-1-methyl-ethyl] 2-oxo-2-phenyl-acetate

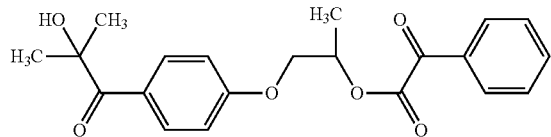 [SMILES: CC(COc1ccc(C(=O)C(C)(C)O)cc1)OC(=O)C(=O)c1ccccc1]

The key intermediate for the title is 2-hydroxy-1-[4-(2-hydroxypropoxy)phenyl]-2-methyl-propan-1-one which is synthesized from 1-phenoxypropan-2-ol in analogy to the synthesis of Irgacure 2959 as described by Koehler, Manfred; Ohngemach, Joerg; Wehner, Gregor; Gehlhaus, Juergen, WO 8605778A1 (1986). White solid, mp 75-76° C.,
$^1$H-NMR (CDCl$_3$, 400 MHz, δ ppm): 8.05 (d, 2 ArH), 6.95 (d, 2 ArH), 4.35 (m, 1H), 4.25 (bs, OH), 4.05-3.90 (m, CH$_2$), 2.45 (s, OH), 1.64 (s, 2×CH$_3$), 1.30 (d, CH$_3$).
This intermediate is esterified with 2-oxo-2-phenyl-acetyl chloride as described in Example 1. The product is isolated as a thick, slightly yellow oil.
$^1$H-NMR (CDCl$_3$, 400 MHz, δ ppm): 8.15-7.00 (m, 9 ArH), 5.70 (m, 1H), 4.25 (m, CH2), 4.20 (bs, OH), 1.70 (s, 2×CH$_3$), 1.60 (d, CH$_3$).

APPLICATION EXAMPLE

Example A1

Photocuring of a Radically Polymerizable Composition

Formulation A: Polyether/Polyester Acrylate Varnish
A photocurable acrylate varnish composition is prepared by mixing the following ingredients:
80% of Laromer PO94F (polyether acrylate containing amino groups, provided by BASF)
20% of Laromer PE9079 (polyester acrylate; provided by BASF)
Formulation B: Epoxy Overprint Varnish
A photocurable epoxy overprint varnish composition is prepared by mixing the following ingredients:
47.8% Laromer LR8986 (aromatic epoxyacrylate; BASF),
38.0% Laromer P077F (polyether acrylate containing amino groups, BASF),
14.0% Laromer DPGDA (tripropylen glycol diacrylate. BASF)
0.2% EFKA 3030 (organically modified polysiloxane levelling agent, EFKA)
The compound to be tested (listed in Table 1 below) is dissolved in the liquid radically curable coating formulation A or in formulation B. This solution is then applied with spreading knife on a white cardboard (100×150 mm, 12 μm wet film thickness). The cardbord specimens are placed in an IST-METZ photocuring apparatus with moving belt and cold mirror reflector and are then photocured by irradiation under air with a mercury low pressure lamp (200 W), mounted 1.5 cm above the belt. The quality of the photocuring is assessed immediately after the irradiation by dry rub resistance (DRR) test: satisfactory curing is achieved when the coated surface is free from any trace after wiping with a paper tissue. Reactivity of the photoinitiator is quantified by the cure speed defined as the maximum belt speed (in m/minute) at which satisfactory cure (passed DRR test) is still obtained.

The results are summarized in Table 1. Table 2 summarizes comparison compounds, tested in the identical formulations.

TABLE 1

| Compound of example No. (weight %) | Radically curable coating composition | Curing speed [m/s] |
|---|---|---|
| 1 (4%) | Formulation A | 80 |
| 1 (4%) | Formulation B | 60 |

TABLE 2

| Compound (weight %) | Radically curable coating composition | Curing speed [m/s] |
|---|---|---|
| Irgacure 184 *$^1$ (4%) | Formulation A | 55 |
| Darocur 1173 *$^2$ (4%) | Formulation A | 65 |
| Irgacure 2959 *$^3$ (4%) | Formulation A | 60 |
| Irgacure 184 *$^1$ (4%) | Formulation B | 55 |

*$^1$ Phenyl-1-hydroxycyclohexyl ketone (provided by BASF)
*$^2$ 2-Hydroxy-2-methyl-1-phenyl-propanone (provided by BASF)
*$^3$ 2-Hydroxy-1-[4-(2-hydroxyethoxy)phenyl]-2-methyl-1-propanone (provided by BASF)

Example A2

Comparison of Volatility

The substantially lower volatility of the inventive compounds is demonstrated by performing the thermogravimetric analysis (TGA). A small sample (about 10 mg) is heated under nitrogen at 10° C./min in the open crucible of the TGA apparatus. A temperature after which 10% of the sample has evaporated is recorded. The higher this temperature is, the lower the volatility is. The results are collected in table 3.

TABLE 3

| Specimen | Temp. until 10% weight loss (° C.) |
|---|---|
| Compound of example 1 | 287 |
| Irgacure 2959 *1 | 216 |
| Dacorur MBF *2 | 134 |
| Darocur 1173 *3 | 113 |

*1 2-Hydroxy-1-[4-(2-hydroxyethoxy)phenyl]-2-methyl-1-propanone (provided by BASF)
*2 methyl-oxo benzeneacetate
*3 2-Hydroxy-2-methyl-1-phenyl-propanone (provided by BASF)

The invention claimed is:

1. A compound of the formula I

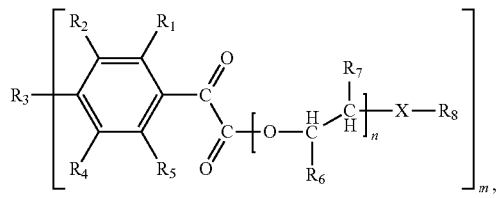

m is 1 or 2;
$R_1$, $R_2$, $R_4$ and $R_5$ independently of one another are hydrogen, $C_1$-$C_4$alkyl, $C_5$-$C_7$cycloalkyl, phenyl, $C_1$-$C_4$alkoxy, $C_5$-$C_7$cycloalkoxy or phenoxy;
$R_3$, if m is 1 has one of the meanings as given above for $R_1$, $R_2$, $R_4$ and $R_5$;
$R_3$, if m is 2 is a divalent group;
$R_6$ is hydrogen or $C_1$-$C_4$alkyl;
$R_7$ is hydrogen, and if $R_6$ is hydrogen then $R_7$ may additionally be $C_1$-$C_4$alkyl;
$R_8$ is group A or B

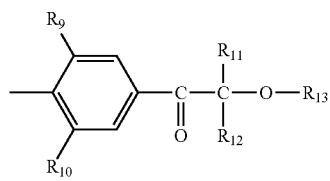

X is —O—, —O—$CH_2$— or —O($CHR_{14}$)—;
n is 0-10;
provided that
(i) if n is 0, and X is O, then $R_8$ is a group A,
(ii) if n is other than 0, then X is O and $R_8$ is the group A,
$R_9$ and $R_{10}$ independently of one another are hydrogen or $C_1$-$C_4$alkyl;
$R_{11}$ and $R_{12}$ independently of one another are $C_1$-$C_4$alkyl or form together with the C atom to which they are attached a 5 to 7 membered saturated carbocyclic ring;
$R_{13}$ is hydrogen, $C_1$-$C_4$alkyl, $C_5$-$C_7$cycloalkyl, 2-tetrahydropyranyl or $Si(C_1$-$C_4$alkyl)$_3$;

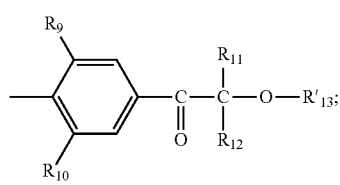

and
$R_{14}$ is a group A'
$R'_{13}$ has one of the meanings as given for $R_{13}$ or is the group C

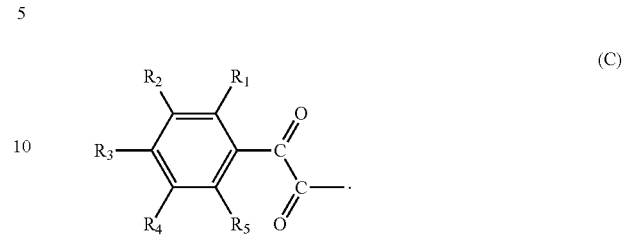

2. The compound according to claim 1, wherein m is 1.
3. The compound according to claim 1, wherein
m is 1;
$R_1$, $R_2$, $R_4$ and $R_5$ are hydrogen;
$R_3$ has one of the meanings as given above for $R_1$, $R_2$, $R_4$ and $R_5$;
$R_6$ is hydrogen or $C_1$-$C_4$alkyl;
$R_7$ is hydrogen;
$R_8$ is group A or B
X is —O—, —O—$CH_2$— or —O($CHR_{14}$)—;
n is 0 or 1;
provided that
(i) if n is 0, and X is O, then $R_8$ is a group A,
(ii) if n is other than 0, then X is O and $R_8$ is the group A,
$R_9$ and $R_{10}$ are hydrogen or $C_1$-$C_4$alkyl;
$R_{11}$ and $R_{12}$ are $C_1$-$C_4$alkyl;
$R_{13}$ is hydrogen;
$R_{14}$ is a group A' and
$R'_{13}$ has one of the meanings as given for $R_{13}$ or is the group C

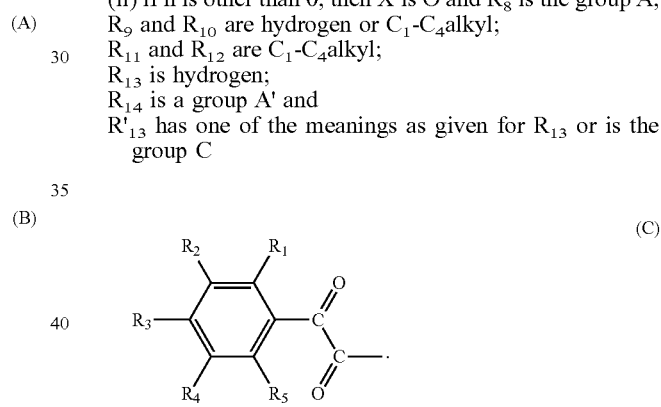

4. A photopolymerizable composition comprising
(A) at least one ethylenically unsaturated photopolymerizable compound and
(B) at least one photoinitiator compound of the formula I according to claim 1.

5. The photopolymerizable composition according to claim 4, which additionally to the component (B) comprises at least one further photoinitiator (C), or further additives (D), or at least one further photoinitiator (C) and further additives (D).

6. The polymerizable composition according to claim 4, which comprises 0.05 to 15% by weight of the at least one photoinitiator compound based on the total composition.

7. The polymerizable composition according to claim 4, which comprises 0.1 to 10% by weight of the at least one photoinitiator compound based on the total composition.

8. A process for the photopolymerization of monomeric, oligomeric or polymeric compounds containing at least one ethylenically unsaturated double bond, which comprises adding to the monomeric, oligomeric or polymeric compounds at least one photoinitiator compound of the formula I according to claim 1 and irradiating the resulting composition with electromagnetic or particulate radiation.

9. A process which comprises utilizing the photopolymerizable polymerizable composition according to claim 4 wherein the process is for the preparation of pigmented and nonpigmented paints and varnishes, powder coatings, printing inks, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, and for image recording materials using microcapsules.

10. The process according to claim 9 wherein the process is for the preparation of pigmented and nonpigmented paints and varnishes, powder coatings, screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, and for image recording materials using microcapsules.

11. A coated substrate coated on at least one surface with the composition according to claim 4.

12. A polymerized or crosslinked composition obtained by curing the polymerizable composition according to claim 4.

13. A process for the preparation of the compound of the formula I as defined in claim 1, which comprises acylating a OH functionalized α-hydroxyketone of the formula III

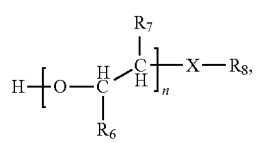

(III)

wherein

X is —O—, —O—CH$_2$— or —O(CHR$_{14}$)—;

n is 0-10;

R$_6$ is hydrogen or C$_1$-C$_4$alkyl;

R$_7$ is hydrogen, and if R$_6$ is hydrogen then R$_7$ may additionally be C$_1$-C$_4$alkyl; with phenyl glyoxylic acid or a derivative of a phenyl glyoxylic acid of the formula IVa or IVb

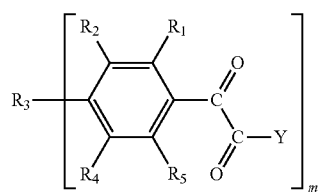

(IVa)

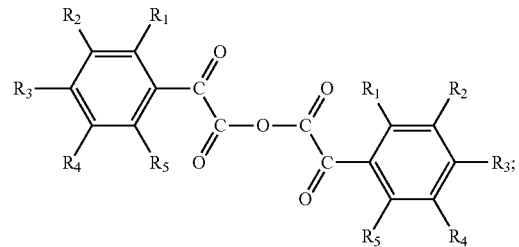

(IVb)

R$_8$ is group A or B

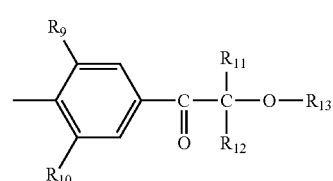

(A)

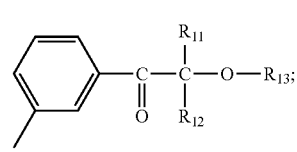

(B)

R$_9$ and R$_{10}$ independently of one another are hydrogen or C$_1$-C$_4$alkyl;

R$_{11}$ and R$_{12}$ independently of one another are C$_1$-C$_4$alkyl or form together with the C atom to which they are attached a 5 to 7 membered saturated carbocyclic ring;

R$_{13}$ is hydrogen, C$_1$-C$_4$alkyl, C$_5$-C$_7$cycloalkyl, 2-tetrahydropyranyl or Si(C$_1$-C$_4$alkyl)$_3$;

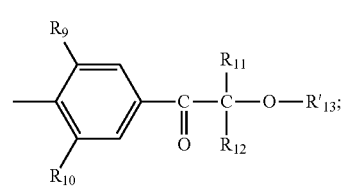

(A')

R$_{14}$ is a group A'

R'$_{13}$ has one of the meanings as given for R$_{13}$ or is the group C

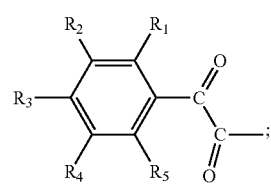

(C)

wherein

R$_1$, R$_2$, R$_4$ and R$_5$ independently of one another are hydrogen, C$_1$-C$_4$alkyl, C$_5$-C$_7$cycloalkyl, phenyl, C$_1$-C$_4$alkoxy, C$_5$-C$_7$cycloalkoxy or phenoxy;

$R_3$, if m is 1 has one of the meanings as given above for $R_1$, $R_2$, $R_4$ and $R_5$;
$R_3$, if m is 2 is a divalent group; and
Y is a OH, Cl or Br, optionally in the presence of a base.

\* \* \* \* \*